United States Patent
Akhavan-Tafti et al.

(10) Patent No.: US 8,389,298 B2
(45) Date of Patent: *Mar. 5, 2013

(54) METHODS USING NOVEL CHEMILUMINESCENT LABELS

(75) Inventors: Hashem Akhavan-Tafti, Howell, MI (US); Renuka De Silva, Northville, MI (US); Wenhua Xie, Novi, MI (US)

(73) Assignee: Lumigen, Inc., Southfield, MI (US)

( * ) Notice: Subject to any disclaimer, the term of this patent is extended or adjusted under 35 U.S.C. 154(b) by 293 days.

This patent is subject to a terminal disclaimer.

(21) Appl. No.: 12/727,651

(22) Filed: Mar. 19, 2010

(65) Prior Publication Data

US 2010/0190271 A1    Jul. 29, 2010

Related U.S. Application Data

(60) Division of application No. 11/724,727, filed on Mar. 16, 2007, now Pat. No. 7,682,839, which is a continuation-in-part of application No. 11/079,899, filed on Mar. 14, 2005, now abandoned.

(51) Int. Cl.
*G01N 33/533* (2006.01)
*G01N 21/76* (2006.01)
*G01N 33/24* (2006.01)

(52) U.S. Cl. ............ 436/546; 436/56; 436/172; 436/80; 436/81

(58) Field of Classification Search .................. None
See application file for complete search history.

(56) References Cited

U.S. PATENT DOCUMENTS

| | | | |
|---|---|---|---|
| 4,104,204 A | 8/1978 | Williams | |
| 4,315,998 A | 2/1982 | Neckers et al. | |
| 5,521,103 A | 5/1996 | Zomer et al. | |
| 5,543,524 A * | 8/1996 | Mattingly et al. | 546/104 |
| 5,656,207 A | 8/1997 | Woodhead et al. | |
| 5,656,500 A | 8/1997 | Law et al. | |
| 5,922,558 A | 7/1999 | Akhavan-Tafti | |
| 6,017,769 A | 1/2000 | Akhavan-Tafti | |
| 6,126,870 A | 10/2000 | Akhavan-Tafti | |
| 6,162,610 A | 12/2000 | Bronstein et al. | 435/7.92 |
| 6,406,913 B1 | 6/2002 | Ullman et al. | |
| 6,545,102 B1 | 4/2003 | Akhavan-Tafti et al. | |
| 6,858,733 B2 | 2/2005 | Akhavan-Tafti et al. | |
| 6,872,828 B2 | 3/2005 | Akhavan-Tafti et al. | |
| 7,186,568 B1 | 3/2007 | Akhavan-Tafti et al. | |
| 7,732,153 B2 * | 6/2010 | Akhavan-Tafti | 435/7.21 |

OTHER PUBLICATIONS

Parejo et al. A transition metal enhance luminol chemiluminescence in the presence of a chelator. Journal of Pharmacological and Toxicological Methods 2000, vol. 43, pp. 183-190.*
Akhavan-Tafti et al. Robust new chemiluminescent perosidase substrates. Medical Device Link. Published May 2004.
R. Handley, H. Akhavan-Tafti, A.P. Schaap, J. Clin. Ligand Assay, (1997), 20(4) 302-312.
L. J. Kricka, Ligand-Binder Assays, Marcel Dekker, Inc., New York, 1985, pp. 15-51.
N. Theodosiou, C. Chalot, C. Ziomek, BioTechniques, (1992) 13(6), 898-901.
T. H Ji, "Bifunctional Reagents," Methods in Enzymology, (1983) 91, 580-609.
F.A. Carey, A.S. Court, J. Org. Chem., (1972) 37, 1926-29.
E.J. Corey and A.P. Kozikowski, Tetrahedron (1975) Lett., 925-8.
I. Shahak and Y. Sasson, Tetrahedron Lett., (1973), 4207-10.
Jerry March, Advanced Organic Chemistry: reactions, Mechanisms, and Structure, 4th ed., Wiley 1992.

* cited by examiner

*Primary Examiner* — Shafiqul Haq
(74) *Attorney, Agent, or Firm* — Richard S. Handley

(57) ABSTRACT

Methods using chemiluminescent label compounds and chemiluminescent labeled conjugates are provided. The compounds comprise an acridan ring bearing an exocyclic ketene dithioacetal group and further contain a labeling substituent which permits attachment to compounds of interest. The novel chemiluminescent compounds and labeled conjugates are convenient to prepare, are highly stable, and generate chemiluminescence rapidly on demand. The compounds and conjugates are useful in assays of an analyte in a sample and in assays employing labeled specific binding pairs.

13 Claims, No Drawings

METHODS USING NOVEL CHEMILUMINESCENT LABELS

CROSS-REFERENCE TO RELATED APPLICATION

The present application is a divisional application of copending U.S. application Ser. No. 11/724,727 filed on Mar. 16, 2007, which is a continuation-in-part of U.S. application Ser. No. 11/079,899, now abandoned, filed on Mar. 14, 2005, herein incorporated by reference.

FIELD OF THE INVENTION

The present invention relates to a new method of rapidly producing chemiluminescence from electron-rich alkenes by a simple chemical process using inexpensive, readily available reagents. The present invention relates further to chemiluminescent labeling compounds, their use in preparing chemiluminescent labeled compounds and the use of the labeled compounds in assay methods. The invention further relates to assay methods for detecting an analyte and for detecting chemiluminescent-labeled analytes. The methods are useful in immunoassays, nucleic acid probe assays and the like.

BACKGROUND OF THE INVENTION

Chemiluminescent detection of analytes has assumed increasing importance in a number of fields, including biomedical analysis, food testing, pathogen identification, forensic investigations and environmental contaminant screening. The means of incorporating a chemiluminescent endpoint into a test or assay can take different forms, such as a chemiluminescent substrate for an enzyme label, a chemiluminescent compound shielded within a structure such as a micelle, liposome or latex particle or by using a chemiluminescent compound as a label. Numerous compounds have been devised for these purposes (R. Handley, H. Akhavan-Tafti, A. P. Schaap, J. Clin. Ligand Assay, 20(4) 302-312 (1997)). The use of chemiluminescent compounds to label species to be detected with small molecules has attracted interest due to the ability to attach multiple labels and to generate the chemiluminescence rapidly. Nevertheless, no single labeling and detection scheme has proven superior in all applications.

Chemiluminescent Labels Luminol, isoluminol and related cyclic diacyl hydrazides were the first chemiluminescent compounds to be adapted as direct labels by modifying their structure to include a linking substituent. Their use is not satisfactory for many applications due to insufficient light generation limiting detection sensitivity. The low chemiluminescence quantum efficiency, 0.1-1%, and times as long as several minutes for all of the photons to be emitted diminish instantaneous light intensity.

Acridinium esters and acridinium sulfonamides have been used extensively in chemiluminescent immunoassays. (See, e.g., U.S. Pat. No. 5,656,500, U.S. Pat. No. 5,521,103 and references cited therein). The principal advantages of these labels are the high yield of chemiluminescence (ca. 10%) coupled with the short duration of emission, typically 1-2 sec. Liberating the light energy in such a short flash creates high light intensities. The use of these labels, however, suffers from certain serious drawbacks. Acridinium esters and to a lesser extent the sulfonamides, are prone to hydrolysis to the nonluminescent carboxylic acid, the hydrolysis being accelerated at alkaline pH. The well-known problem of pseudobase formation from attack of water at the 9 position on the ring requires a separate reaction step to regenerate the acridinium ring.

Ruthenium or osmium-containing complexes produce chemiluminescence when oxidized electrochemically in the presence of a sacrificial amine electron donor. The reaction requires a more costly and complex instrument for performing the electrochemical and light detection steps simultaneously.

U.S. Pat. Nos. 6,017,769 and 6,126,870 disclose a class of acridan compounds with heterosubstituted double bonds and a reactive linking group as chemiluminescent labels. Exemplary compounds contain a vinyl phosphate moiety. No examples of compounds bearing two sulfur substituents on the double bond were disclosed.

U.S. Pat. Nos. 6,858,733 and 6,872,828 disclose acridan ketenedithioacetal compounds as chemiluminescent substrates for peroxidase enzymes.

U.S. Pat. No. 7,186,568 discloses acridan compounds that undergo an electrochemical oxidation at an electrode to produce electrochemiluminescence for use in detection. In one embodiment the acridan compound can have a heterosubstituted double bond and a reactive linking group for use as a chemiluminescent label. Exemplary compounds contain a vinyl phosphate moiety. No examples of compounds bearing two sulfur substituents on the double bond were disclosed.

U.S. Pat. No. 6,046,913 discloses methods for determining an analyte under conditions such that the analyte brings a photosensitizer and a chemiluminescent compound into close proximity. The photosensitizer generates singlet oxygen and activates the chemiluminescent compound when it is in close proximity to produce light. In preferred embodiments the photosensitizer and/or the chemiluminescent compound is associated with a latex particle or oil droplet having a bound specific binding pair member.

While many large molecules are used as labels, including enzymes and the photoprotein aequorin, their use suffers the disadvantage of limiting the number of labels which can be attached to the target species and having the tendency of depositing non specifically on supports and surfaces.

It remains a goal of the assay field to develop chemiluminescent labeling compounds which are small, water soluble molecules, have high chemiluminescence efficiencies, emit the light rapidly upon reaction with simple chemical activating agents, are stable on extended storage and not subject to side reactions. The present invention provides such compounds.

Labeling Procedures. A wide variety of procedures for chemically binding labels to organic and biological molecules are described in the literature (see, for example: L. J. Kricka, Ligand-Binder Assays, Marcel Dekker, Inc., New York, 1985, pp. 15-51 and M. Z. Atassi, "Chemical Modification and Cleavage of Proteins," Chapter 1 in Immunochemistry of Proteins, Vol. 1, Plenum Press, New York, 1977, pp. 1-161, and references therein). Antibodies and proteins are conveniently labeled by reaction of certain nucleophilic groups present in proteins (—SH, —OH, —NH2, —COOH) with chemically reactive groups. Appropriately functionalized nucleic acids and DNA probes can also be labeled by reaction with the corresponding reactive group on a label. Many other types of molecules which can be labeled including antibodies, enzymes, protein antigens, peptides, haptens, steroids, carbohydrates, fatty acids, hormones, nucleosides and nucleotides.

Chemiluminescent Detection in Gels. A method for the detection of the enzyme alkaline phosphatase in a gel using a chemiluminescent substrate has been described (N. Theodosiou, C. Chalot, C. Ziomek, BioTechniques, 13(6), 898-901(1992)). The aforementioned U.S. Pat. Nos. 6,017,769 and 6,126,870 disclose chemiluminescent labeling compounds which can be detected as a label on a compound in an electrophoresis gel.

SUMMARY OF THE INVENTION

It is an object of the present invention to provide methods for generating chemiluminescence from a chemiluminescent labeled compound by a simple chemical process using inexpensive, readily available reagents.

It is a further object of the present invention to provide labeling compounds for preparing chemiluminescent labeled compounds.

It is another object of the present invention to provide chemiluminescent labeled compounds.

It is also an object of the present invention to provide labeling compounds of formula I wherein one of the groups $R^1$-$R^{11}$ is a labeling substituent.

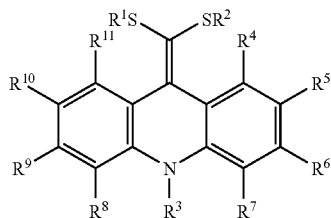

I

General Description

Modern biomedical analyses require the ability to detect very small amounts of compounds due either to low abundance of the analyte in the sample or to limited sample quantity. In addition it must be possible to detect the quantity of the compound precisely over a very wide range of concentrations. Chemiluminescent labeling compounds and methods are disclosed herein which are suitable for these types of analyses.

The present invention relates generally to methods of generating chemiluminescence and compounds for use in these methods. The methods use acridan compounds and simple, inexpensive and readily available reagents for generating chemiluminescence therefrom and are the result of chemical as opposed to electrochemical reactions. No electrodes, electrochemical equipment or sources of electrical current are used in the reaction. The light producing reaction can be used for a number of art-recognized purposes, including analytical methods of assay, signaling, emergency lighting and novelty items.

The present invention also involves chemiluminescent labeling compounds which can be bound to organic and biological molecules by chemical bonds or through physical interactions for the purpose of performing an assay. Reaction of the chemiluminescent compounds of the present invention according to the presently described methods produces chemiluminescence as visible light. The intensity of the resulting chemiluminescence provides a direct measure of the quantity of the chemiluminescent label and, therefore, of the labeled compound.

The present invention further involves a method for detecting a chemiluminescent labeled compound in an electrophoresis gel of the type used in separating biological molecules. Chemiluminescent labeled compounds of the present invention can be applied to a gel, separated electrophoretically and subsequently be detected in the gel without the need for transfer to a blotting membrane.

The acridan compounds useful in the methods of the invention have formula I

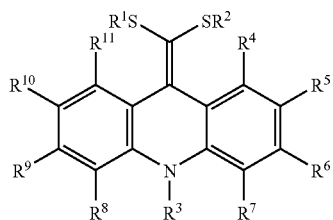

wherein at least one of the groups $R^1$-$R^{11}$ is a labeling substituent of the formula -L-RG wherein L is a linking group which can be a bond or another divalent or polyvalent group, RG is a reactive group which enables the chemiluminescent labeling compound to be bound to another compound, $R^1$, $R^2$ and $R^3$ are organic groups containing from 1 to 50 non-hydrogen atoms, and each of $R^4$-$R^{11}$ is hydrogen or a noninterfering substituent.

DESCRIPTION OF THE PREFERRED EMBODIMENTS

Definitions

Acid—A compound which, when added to water, causes a decrease in the pH of the resulting solution. Acid as used herein includes mineral acids, such as hydrochloric, nitric, sulfuric and perchloric, organic acids, including carboxylic acids such as oxalic, acetic and propionic, and other types of organic compounds, such as picric acid and Lewis acids, such as aluminum chloride, ferric chloride and the like.

Alkyl—A branched, straight chain or cyclic hydrocarbon group containing from 1-20 carbons. Lower alkyl as used herein refers to those alkyl groups containing up to 8 carbons.

Alkenyl—A branched, straight chain or cyclic hydrocarbon group containing at least one C—C double bond and containing from 2-20 carbons. Lower alkenyl as used herein refers to those alkenyl groups containing up to 8 carbons.

Alkynyl—A branched or straight chain hydrocarbon group containing at least one C—C triple bond and containing from 2-20 carbons. Lower alkynyl as used herein refers to those alkynyl groups containing up to 8 carbons.

Analyte—A substance the presence or amount of which is to be measured in a sample by an assay. Analytes include organic and biological molecules to which a specific binding partner having a specific binding affinity exists. Exemplary analytes include, without limitation, single stranded or double stranded DNA, RNA, DNA-RNA complexes, oligonucleotides, antibodies, antibody fragments, antibody DNA chimeras, antigens, haptens, proteins, lectins, avidin, streptavidin and biotin. Other exemplary analytes also include drugs, hormones and pesticides.

Aryl—An aromatic ring-containing group containing 1 to 5 carbocyclic aromatic rings, which can be substituted with 1 or more substituents other than H.

Biomedical analysis—Analyses of samples of biological origin for analytes of interest. The analyses can be immunoassays, western blots, northern blots, Southern blots, DNA hybridization assays, DNA sequence analysis, colony hybridizations, gene expression analysis, high throughput drug screening, detection of infectious agents or pathogens and the like.

Glycosyl—Residues of carbohydrate groups including hexoses and pentoses and contain one or more sugar unit. Examples include fructose, galactose, glucose, glucuronate, mannose, ribose, N-acetylglucosamine and the like.

Halogen—Fluorine, chlorine, bromine or iodine atoms.

Heteroaryl—An aromatic ring-containing group containing 1 to 5 carbocyclic aromatic rings in which at least one of the ring carbon atoms is replaced with a nitrogen, oxygen or sulfur atom and which can be substituted with 1 or more substituents other than H.

Luminescent—capable of emitting light when excited to an electronic excited state. The light can be emitted either as fluorescence when decaying from a singlet excited state or as phosphorescence when decaying from a triplet excited state.

Peroxide—A compound containing an O—O bond, preferably hydrogen peroxide or a complex of hydrogen peroxide such as urea peroxide, perborate or percarbonate.

Sample—A fluid containing or suspected of containing one or more analytes to be assayed. Typical samples which are analyzed by the chemiluminescent reaction method are biological samples including body fluids such as blood, plasma, serum, urine, semen, saliva, cell lysates, tissue extracts and the like. Other types of samples include food samples and environmental samples such as soil or water.

Specific binding pair—Two substances which exhibit a mutual binding affinity. Examples include antigen-antibody, hapten-antibody or antibody-antibody pairs, complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

Substance labeled with a labeling compound, labeled substance, labeled compound—all refer to a conjugate of a molecule and one or more copies of a chemiluminescent label of the invention. The molecule can be e.g. an analyte in an assay, a specific binding pair member or a tracer compound.

Substituted—Refers to the replacement of at least one hydrogen atom on a group by another atom or a group having from 1 to 50 atoms selected from C, O, N, S, P, Si, B, Se, F, Cl, Br and I. It should be noted that in references to substituted groups it is intended that multiple points of substitution can be present unless indicated otherwise.

It has been discovered that chemiluminescent compounds of formula I above containing a labeling substituent undergo a reaction with certain reagents to generate chemiluminescence as a brief, intense flash of light. Use of the present compounds for detection, e.g. as labels, in chemiluminescent assays leads to highly sensitive detection of analytes. In one embodiment chemiluminescent compounds of the present invention have formula I above wherein $R^1$, $R^2$ and $R^3$ are organic groups containing from 1 to 50 non-hydrogen atoms selected from C, N, O, S, P and halogen atoms, wherein $R^1$ and $R^2$ can be joined together in a ring, $R^4$-$R^{11}$ are independently selected from hydrogen and substituents which do not interfere with the generation of chemiluminescence, and at least one of the groups $R^1$-$R^{11}$ is a labeling substituent -L-RG where L is a linking group and RG is a reactive group. The labeling substituent -L-RG is present preferably on one of $R^1$ or $R^2$ although it can also be present as a substituent on $R^3$ or one of $R^4$-$R^{11}$.

Chemiluminescent Labeling Compounds. The groups $R^1$ and $R^2$ can be any organic group containing from 1 to about 50 non-hydrogen atoms selected from C, N, O, S, P, Si and halogen atoms which allows or does not interfere with light production. By the latter is meant that when a compound of formula I undergoes a reaction of the present invention, the light is produced and can involve the production of one or more chemiluminescent intermediates. $R^1$ and $R^2$ are preferably selected from substituted or unsubstituted alkyl, substituted or unsubstituted alkenyl, substituted or unsubstituted alkynyl, substituted or unsubstituted aryl, and substituted or unsubstituted aralkyl groups of 1-20 carbon atoms. When $R^1$ or $R^2$ is a substituted group, it is substituted with 1-3 atoms or groups selected from carbonyl groups, carboxyl groups, tri ($C_1$-$C_8$ alkyl)silyl groups, an $SO_3^-$ group, an $OSO_3^{-2}$ group, glycosyl groups, a $PO_3^-$ group, an $OPO_3^{-2}$ group, halogen atoms, a hydroxyl group, a thiol group, amino groups, quaternary ammonium groups, or quaternary phosphonium groups. In a preferred embodiment, $R^1$ or $R^2$ is preferably substituted with the labeling substituent of the formula -L-RG where L is a linking group and RG is a reactive group.

The group $R^3$ is an organic group containing from 1 to 50 atoms non-hydrogen atoms selected from C, N, O, S, P, Si and halogen atoms in addition to the necessary number of H atoms required satisfy the valencies of the atoms in the group. More preferably $R^3$ contains from 1 to 20 non hydrogen atoms. The organic group is preferably selected from the group consisting of alkyl, substituted alkyl, substituted or unsubstituted alkenyl, substituted or unsubstituted alkynyl, substituted or unsubstituted aryl, and substituted or unsubstituted aralkyl groups of 1-20 carbon atoms. More preferred groups for $R^3$ include substituted or unsubstituted $C_1$-$C_4$ alkyl groups, phenyl, substituted or unsubstituted benzyl groups, alkoxyalkyl, carboxyalkyl and alkylsulfonic acid groups. When a substituent group is itself substituted, e.g. a substituted alkyl group, it will have 1-3 of the hydrogen atoms in the C—H bonds replaced by another atom or group selected from the same list of substituents. The group $R^3$ can be joined to either $R^7$ or $R^8$ to complete a 5 or 6-membered ring. In one embodiment, $R^3$ is substituted with the labeling substituent of the formula -L-RG.

In the compounds of formula I, the groups $R^4$-$R^{11}$ each are independently H or a substituent group which permits the light to be produced and generally contain from 1 to 50 atoms selected from C, N, O, S, P, Si and halogen atoms. Representative substituent groups which can be present include, without limitation, alkyl, substituted alkyl, aryl, substituted aryl, aralkyl, alkenyl, alkynyl, alkoxy, aryloxy, halogen, amino, substituted amino, carbonyl, carboxyl, carboalkoxy, carboxamide, cyano, and sulfonate groups. When a substituent group is itself substituted, e.g. a substituted alkyl group, it will have 1-3 of the hydrogen atoms in the C—H bonds replaced by another atom or group selected from the same list of substituents. Pairs of adjacent groups, e.g. $R^4$-$R^5$ or $R^5$-$R^6$, can be joined together to form a carbocyclic or heterocyclic ring system comprising at least one 5 or 6 membered ring which is fused to the ring to which the two groups are attached. Such fused heterocyclic rings can contain N, O or S atoms and can contain ring substituents other than H such as those mentioned above. One or more of the groups $R^4$-$R^{11}$ can be a labeling substituent of the formula -L-RG. It is preferred that $R^4$-$R^{11}$ are selected from hydrogen, halogen and alkoxy groups such as methoxy, ethoxy, t-butoxy and the like. In one preferred group of compounds one of $R^4$-$R^{11}$ is selected from hydrogen, halogen and alkoxy groups and the other of $R^4$-$R^{11}$ are hydrogen atoms. Another preferred group of compounds has one of $R^5$, $R^6$, $R^9$ or $R^{11}$ as a halogen and the other of $R^4$-$R^{11}$ are hydrogen atoms.

Substituent groups can be incorporated in various quantities and at selected ring or chain positions in the acridan ring in order to modify the properties of the compound or to provide for convenience of synthesis. Such properties include, e.g. chemiluminescence quantum yield, rate of reaction with the enzyme, maximum light intensity, duration of light emission, wavelength of light emission and solubility in the reaction medium. Specific substituents and their effects are illustrated in the specific examples below, which, however, are not to be considered limiting the scope of the invention in any way. For synthetic expediency compounds of formula I may have each of $R^4$-$R^{11}$ as a hydrogen atom.

Linking group (L). The linking group can be a bond, an atom, divalent groups and polyvalent groups, or a straight, or branched chain of atoms some of which can be part of a ring structure. The substituent usually contains from 1 to about 50 non-hydrogen atoms, more usually from 1 to about 30 non-hydrogen atoms. Atoms comprising the chain are selected from C, O, N, S, P, Si, B, and Se atoms, preferably from C, O, N, P and S atoms. Halogen atoms can be present as substituents on the chain or ring. Typical functional groups comprising the linking substituent include alkylene, arylene, alkenylene, ether, peroxide, carbonyl as a ketone, ester, carbonate ester, thioester, or amide group, amine, amidine, carbamate, urea, imine, imide, imidate, carbodiimide, hydrazine, diazo, phosphodiester, phosphotriester, phosphonate ester, thioether, disulfide, sulfoxide, sulfone, sulfonate ester, sulfate ester, and thiourea groups.

Reactive group. The reactive group RG is an atom or group whose presence facilitates bonding to another molecule by covalent attachment or physical forces. In some embodiments, attachment of a chemiluminescent labeling compound of the present invention to another compound will involve loss of one or more atoms from the reactive group for example when the reactive group is a leaving group such as a halogen atom or a tosylate group and the chemiluminescent labeling compound is covalently attached to another compound by a nucleophilic displacement reaction. In other embodiments, attachment of a chemiluminescent labeling compound to another compound by covalent bond formation will involve reorganization of bonds within the reactive group as occurs in an addition reaction such as a Michael addition or when the reactive group is an isocyanate or isothiocyanate group. In still other embodiments, attachment will not involve covalent bond formation, but rather physical forces in which case the reactive group remains unaltered. By physical forces is meant attractive forces such as hydrogen bonding, electrostatic or ionic attraction, hydrophobic attraction such as base stacking, and specific affinity interactions such as biotin-streptavidin, antigen-antibody and nucleotide-nucleotide interactions.

TABLE 1

Reactive Groups for Chemical Binding of Labels to Organic and Biological Molecules a.) Amine reactive groups.

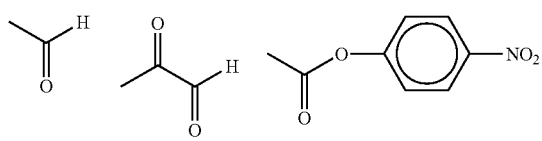

TABLE 1-continued

Reactive Groups for Chemical Binding of Labels to Organic and Biological Molecules

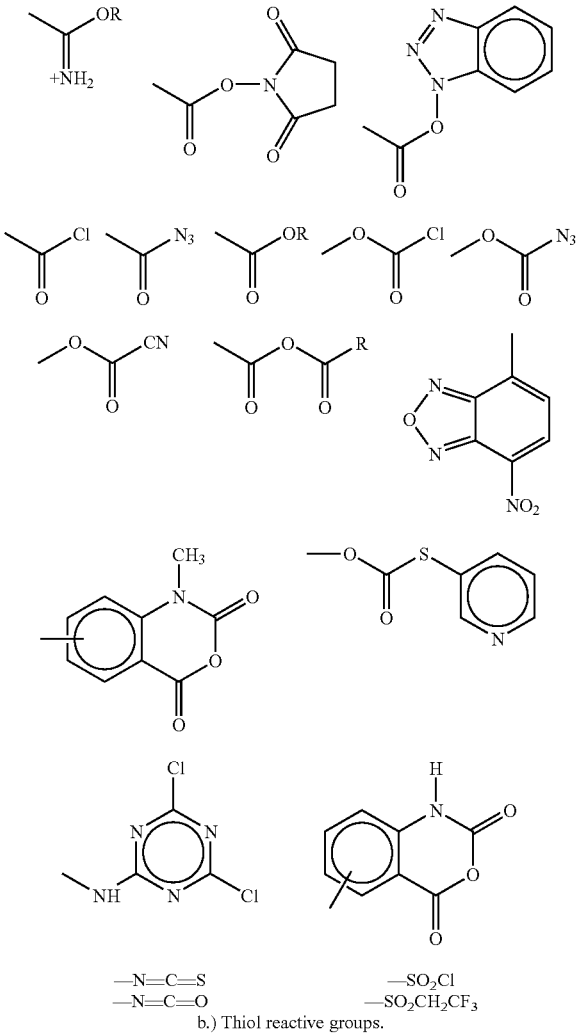

b.) Thiol reactive groups.

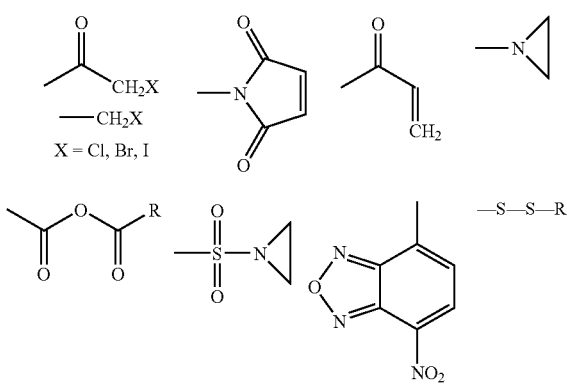

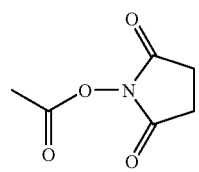

TABLE 1-continued

Reactive Groups for Chemical Binding of
Labels to Organic and Biological Molecules 3) Carboxylic acid reactive groups.

4) Hydroxyl reactive groups.

5) Aldehyde/ketone reactive groups.

—NH₂   —ONH₂   —NHNH₂

6) Other reactive group pairs.

Preferred reactive groups include OH, NH$_2$, ONH$_2$, NHNH$_2$, COOH, SO$_2$CH$_2$CF$_3$, N-hydroxysuccinimide ester, N-hydroxy succinimide ether and maleimide groups.

Bifunctional coupling reagents can also be used to couple labels to organic and biological molecules with moderately reactive groups (see L. J. Kricka, *Ligand-Binder Assays*, Marcel Dekker, Inc., New York, 1985, pp. 18-20, Table 2.2 and T. H Ji, "Bifunctional Reagents," *Methods in Enzymology*, 91, 580-609 (1983)). There are two types of bifunctional reagents, those which become incorporated into the final structure e.g. glutaraldehyde, and those which do not and serve only to couple the two reactants, e.g. carbodiimides such as DCC and EDAC.

In another embodiment the labeling compounds have formula II wherein each of R$^4$-R$^{11}$ are hydrogen. The groups R$^1$, R$^2$ and R$^3$ are as defined above.

II

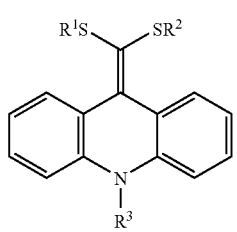

In another embodiment the labeling compounds have formulas III or IV.

III

IV

In another embodiment the labeling compounds have formula V.

V

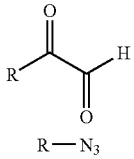

In another embodiment, the invention relates to chemiluminescent labeled compounds. By this is meant conjugates of a compound to be detected and at least one moiety comprising a chemiluminescent labeling compound of any of formulas I-V. When preparing a conjugate using a labeling compound of formula I-V, the compound to be labeled with the chemiluminescent label will become attached by means of the reactive group RG. The attachment may result in the displacement of a portion of the reactive group RG. For example when an N hydroxysuccinimide ester is RG, the N-hydroxysuccinimide portion is lost in forming the link. In other cases, RG is intact as for example when it is a maleimide group reacting with an —SH group on a compound being labeled or an isocyanate reacting with an amine or —OH group. In still other cases, the entire RG is lost in forming the link; an example would be when RG is a leaving group such as a halide, azide, or p-toluenesulfonate.

When preparing the chemiluminescent labeled compound, a molar excess of the chemiluminescent labeling compound is typically used although it is not necessary. The chemiluminescent labeling compound is preferably used in at least 5-fold molar excess to the compound to be labeled and usually in at least a 1-fold molar ratio. The chemiluminescent labeled compound may be labeled with one labeling group or multiple copies of the group. In general it is desirable to incorporate multiple labels to increase the amount of signal which can be generated.

Synthetic Methods. Compounds of formula I can be prepared by various methods. In a preferred method compound I can be prepared by reacting the enolate of a dithioester with a reagent of the formula $R^1$-LG where LG represents a leaving group as exemplified by the scheme below.

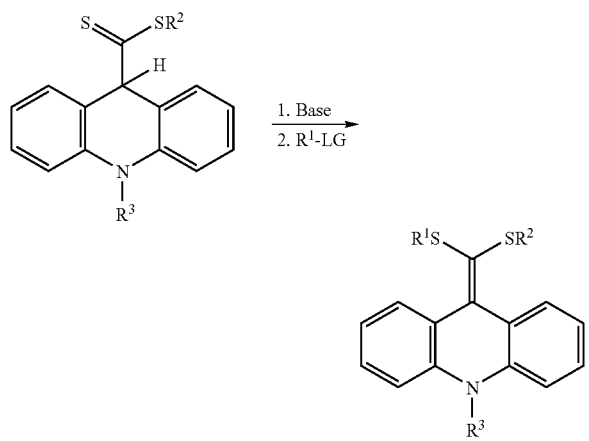

Typical leaving groups include halogens, such as chloride, bromide and iodide, sulfonates such as methanesulfonate, p-toluenesulfonate and trifluoromethanesulfonate, carboxylates such as acetate and benzoate, sulfates such as methosulfate, and other groups such as imidazole, triazole and tetrazole, maleimide, succinimidoxy groups. The dithioester precursor can be prepared by reacting an acridan carbanion with carbon disulfide followed by S-alkylation.

Methods of preparing compounds of formula I also include nucleophilic addition of a lithiosilane compound or a phosphorus ylide to a suitable carbonyl compound according to the two schemes below (F. A. Carey, A. S. Court, J. Org. Chem., 37, 1926-29, (1972)).

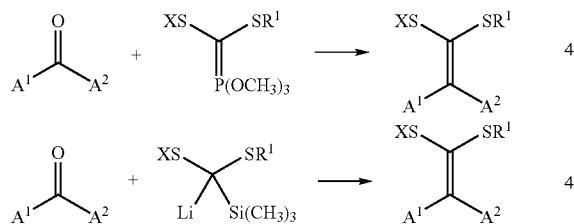

In another method, an ester is converted to a ketene dithioacetal by reaction with a bis(dialkylaluminum) dithiol reagent as disclosed in E. J. Corey and A. P. Kozikowski, Tetrahedron Lett., 925-8 (1975) and shown below.

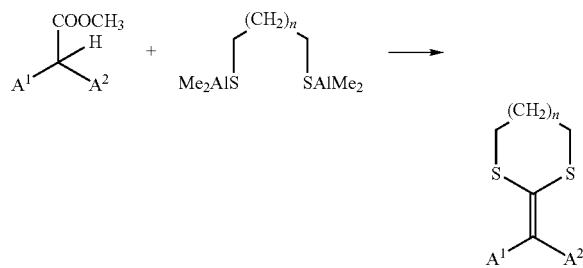

In yet another method, an anion of an active methylene group is reacted with $CS_2$ and the dithiocarboxylate is reacted with a reagent $R^1$-LG containing the $R^1$ group to form a dithioester. An example of the latter methodology is disclosed in I. Shahak and Y. Sasson, Tetrahedron Lett., 4207-10 (1973). The dithioester is converted to the enolate and reacted with a reagent of the formula X-LG.

Methods of preparing chemiluminescent labeling compounds generally involve preparing a precursor compound of formula I and subjecting it to one or more additional reactions, generally known to the skilled artisan, to provide a labeling substituent appended to one of the groups $R^1$-$R^{11}$, preferably $R^1$ or $R^2$. Numerous examples are provided below to illustrate the general principle.

Methods of Generating Chemiluminescence. In one embodiment the present invention relates to methods for producing chemiluminescence comprising subjecting a labeled substance to nonelectrochemical conditions for producing chemiluminescence from the label moiety. In particular the methods are applied in the service of assay methods for detecting an analyte in a sample.

In one embodiment of a method of producing chemiluminescence from a labeling compound of formula I or a substance labeled with a labeling compound of formula I, the compound is reacted with singlet oxygen, $^1O_2$ to produce an intermediate that generates chemiluminescence.

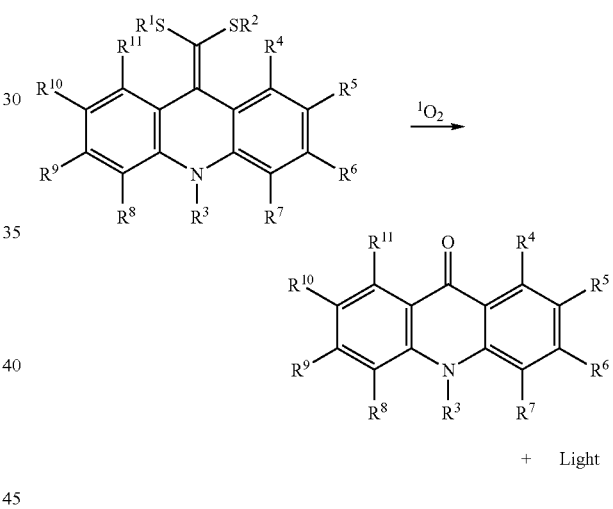

In one embodiment singlet oxygen is generated photochemically by irradiating a photosensitizer in the presence of molecular oxygen in a solvent. The photosensitized generation of singlet oxygen is performed in the presence of the labeling compound or the compound labeled with the labeling compound. Soluble photosensitizers for the photosensitized generation of singlet oxygen are known in the art. U.S. Pat. Nos. 4,104,204 and 4,315,998 for example disclose several photosensitizers including Rose Bengal, Eosin Y, Alizarin Red S, Congo Red, and Orange G. Also useful are fluorescein dyes, rhodamine dyes, Erythrosin B, chlorophyllin trisodium salt, salts of hemin, hematoporphyrin, Methylene Blue, Crystal Violet and Malachite Green, tetraphenylporphyrin (TPP), metal complexes of TPP, especially zinc and manganese, and $C_{60}$. Polymer-immobilized photosensitizers may also be employed. Such immobilized photosensitizers are disclosed in U.S. Pat. Nos. 4,104,204; 4,315,998 and 6,545,102. Alternatively, singlet oxygen can be generated chemically by thermolysis of triphenylphosphite ozonide, naphthalene endoperoxides, or anthracene endoperoxides according to methods known in the art of singlet oxygenations. In another embodiment singlet oxygen can be produced in situ by a chemical reaction. Exemplary chemical reactions producing singlet oxygen include the reaction of hypochlorite ion with hydrogen peroxide, bromine and hydrogen peroxide, percarboxlic acids and base, as well as potassium chromate and hydrogen peroxide. Reactions are desirably performed in the presence of a liquid medium to permit transfer of the singlet oxygen and allow contact with the label.

Without wishing to be bound by any particular theory, it is thought that reaction of a compound of formula I with singlet oxygen may result in the formation of a 1,2-dioxetane compound that undergoes a chemiluminescent fragmentation reaction according to the customary reaction path for such dioxetane compounds. It has been observed that such chemiluminescent decomposition of the photooxygenation product of a compound of formula I occurs rapidly even at temperatures below room temperature. In one embodiment the chemiluminescent reaction is performed at or near room temperature in which case the chemiluminescent light is emitted immediately while the reaction with singlet oxygen is taking place. When it is desired to detect the emitted light it can be done during the reaction with singlet oxygen. Photosensitized generation of singlet oxygen requires irradiation of the photosensitizing dye with light in the visible wavelengths. Nevertheless this irradiation can be performed simultaneous with the detection of the emitted chemiluminescent light. This is possible since the wavelength range of emission is distinct from the wavelength of light used to excite the photosensitizer. In most cases chemiluminescence is emitted at wavelengths significantly shorter than the exciting light, often by 100-200 nm. A simple optical filter or monochromator will permit the necessary differentiation. In another embodiment irradiation of the sensitizer can be performed intermittently or in pulsed "off-on" fashion and the chemiluminescence detected during the intervals when irradiation is not taking place. In an alternative embodiment the photooxygenation can be performed at a temperature low enough to delay production of chemiluminescence. After a suitable time, irradiation is discontinued and the sample is warmed up to initiate light emission.

In another embodiment for producing chemiluminescence from a labeling compound of formula I or a compound labeled with a labeling compound of formula I, the labeling compound or labeled compound is reacted with a peroxidase and a peroxide. The peroxidase will be present in excess and the labeled compound will be the limiting reagent. In contrast, methods disclosed in Applicants' earlier patents including U.S. Pat. Nos. 5,922,558; 6,858,733; 6,872,828 describe chemiluminescent reactions of acridan compounds with a peroxide and a peroxidase where the peroxidase is the limiting reagent and the acridan is present in great excess. In the latter methods the primary goal is to detect very small quantities of a peroxidase or a conjugate or a peroxidase and some substance to be detected. Enzymatic turnover of substrate by the enzyme permits quantities on the order of 1 attomol ($10^{-18}$ mol) of peroxidase to be detected. The acridan substrate is typically used at a concentration of 0.1-1 mmol ($10^{-3}$-$10^{-4}$ mol) in order to satisfy the requirements for enzymatic functioning and for the reaction rate to reach steady state. Light emission is then produced as a steady "glow". The ratio of acridan to enzyme under these conditions can be up to $10^{15}$. In the present method, the relative amounts of acridan compound and peroxidase are quite different. In embodiments where the acridan compound is present as a label in an assay, it can be present in very low amount, on the order of 1 attomol ($10^{-18}$ mol) since it is desirable to be able to detect the smallest possible amount of labeled compound. The peroxidase is provided in much greater relative proportion, since it is to be used as a reagent rather than as a catalyst. The ratio of acridan to enzyme under these conditions can be from approximately 100:1 to 1:1000, more commonly from 10:1 to about 1:100. The difference in the acridan/peroxidase ratio between the two methods can span from 15-20 orders of magnitude. The tremendously lower relative amount of acridan compound notwithstanding, significant light intensities can be produced. The chemiluminescence signal is produced as a brief flash of light, typically lasting only a few seconds or less and usually not more than about five seconds.

The peroxide is supplied at a concentration of $10^{-6}$ M to $10^{-1}$ M, typically in aqueous solution. In one embodiment the peroxidase is added to a reaction system containing the labeling compound or substance labeled therewith and the peroxide is introduced to produce the chemiluminescent signal. In other embodiments the peroxide and peroxidase can be introduced simultaneously or pre-mixed and added simultaneously. The peroxide can be hydrogen peroxide, or a complex of hydrogen peroxide such as urea peroxide, perborate salts or percarbonate salts.

In another embodiment for producing chemiluminescence from a labeling compound of formula I or compound labeled with the labeling compound, the labeling compound or labeled substance is reacted with a peroxide and a transition metal compound selected from transition metal ions, salts, or complexes. Preferred transition metal ions include $Fe^{+2}$, $Fe^{+3}$, $Co^{+2}$, $Co^{+3}$, $Cu^{+2}$, $Ni^{+2}$, $Cr^{+3}$, $Zn^{+2}$ and $Mn^{+2}$. The metal ion can be present as the free ion or as a complex with an organic ligand. When present as a salt, it can be provided as a halide salt, such as a chloride, bromide or iodide, a nitrate, acetate or other soluble salt. The peroxide and transition metal salt are preferably present in solutions. Aqueous solutions are desirable. The transition metal is supplied at a concentration of $10^{-6}$ to $10^{-1}$ M. The peroxide is supplied at a concentration of $10^{-6}$ to $10^{-1}$ M, typically in aqueous solution. In one embodiment a solution of the transition metal salt is added to a reaction system containing the labeling compound or substance labeled therewith and the peroxide is introduced to produce the chemiluminescent signal. In other embodiments the peroxide and transition metal salt can be introduced simultaneously or pre-mixed and added simultaneously. The chemiluminescence signal is produced as a brief flash of light, typically lasting only a few seconds or less and usually not more than about five seconds.

In another embodiment, reaction components may be supplied as solutions containing auxiliary components such as buffers, surfactants and fluorescent compounds. Preferred buffers have a pH of approximately 5 to 9. Surfactants include anionic, nonionic and cationic surfactants. Nonionic surfactants useful in the practice of the present invention include by way of example polyoxyethylenated alkylphenols, polyoxyethylenated alcohols, polyoxyethylenated ethers and polyoxyethylenated sorbitol esters. Cationic surfactants include quaternary ammonium salt compounds such as CTAB. In a further embodiment, fluorescent energy acceptors can be employed to shift the maximum emission to longer wavelengths (red-shifting) and/or to increase the quantity of luminescence emitted. Fluorescers can be covalently linked to a compound of formula I or, alternatively, can be added to the reaction solution as separate species, or linked to a soluble polymer or electrostatically associated with a micelle or soluble polymer.

Chemiluminescent Assay Methods. Another embodiment of the present invention is the use of the above chemiluminescent reactions in a method to detect the presence, location or amount of an analyte in a sample comprising providing a substance labeled with a compound of formula I, generating the light by the chemiluminescent reaction with the labeled compound, detecting the light produced and, if quantitation is desired, measuring the amount of light, and relating the presence, location or amount of light produced to the presence, location or amount of the analyte. The relationship between light intensity and amount of analyte can be easily discerned by constructing a calibration curve with known amounts of the chemiluminescent compound.

Analytes. Substances that can be assayed by employing the present chemiluminescent methods in an assay procedure include various classes of organic and biological molecules. In one embodiment such assays can involve the use of a specific binding reaction between at least one pair of specific binding partners, one of which is the analyte. At least one of the specific binding partners is labeled with a compound of formula I in the manner described above. In one embodiment the chemiluminescent compound may be bound to the analyte. A specific binding partner for the analyte can be used to capture the labeled analyte in order to fix its position, or to purify it from other sample components, or to concentrate it in a medium, or to determine the amount of labeled or unlabeled analyte. In another embodiment the chemiluminescent compound may be bound to a sbp member that is capable of binding directly or indirectly to the analyte. The term "capable of binding directly or indirectly" means that the designated entity can bind specifically to the entity (directly) or can bind specifically to a specific binding pair member or to a complex of two or more sbp members which is capable of binding the other entity (indirectly).Exemplary analytes include drugs, hormones, pesticides, pesticide metabolites, DNA, RNA, oligonucleotides, antibodies, antibody fragments, antibody-DNA chimeras, antigens, haptens, proteins, carbohydrates, lectins, receptors, avidin, streptavidin and biotin. Exemplary binding partners include antigen-antibody, hapten-antibody or antibody-antibody pairs, complementary oligonucleotides or polynucleotides, avidin biotin, streptavidin-biotin, hormone-receptor, lectin carbohydrate, IgG-protein A, nucleic acid-nucleic acid binding protein and nucleic acid-anti-nucleic acid antibody.

In another embodiment a labeled compound comprising a substance labeled with a compound of formula I can be a tracer compound. Such compounds may find use in examining the fate or spatial distribution of a substance in the environment, in a fluid supply vessel such as a pipe, or in a bacterial, plant or animal organism. In this embodiment a labeled tracer compound is provided and allowed to distribute within the test system. One of the three disclosed reagents, singlet oxygen, peroxide/peroxidase, or transition metal/peroxide is administered, and the location and/or amount of light produced is detected.

In another embodiment the present methods are used in the service of an immunoassay. The analyte hapten, antigen or antibody is assayed by detecting the presence or amount of a chemiluminescent-labeled specific binding partner for the analyte or a labeled analog of the analyte. Various assay formats and the protocols for performing the immunochemical steps of immunoassays are well known in the art. These assays fall broadly into two categories. Competitive assays feature an immunological binding of a specific antibody with the analyte and an analyte analog, e.g. a detectably labeled analyte molecule. Sandwich assays result by the sequential or simultaneous binding of two antibodies, one of which is detectably labeled, with the analyte. The detectably labeled binding pair so formed can be assayed with the compounds and methods of the present invention. Measurement can be performed with labeled species attached to a solid surface or support including beads, tubes, microwells, magnetic particles, latex particles, silica particles, test strips, membranes and filters such as are in common use in the art.

In another embodiment the present methods are used in the detection of nucleic acids by the use of labeled nucleic acid probes. Methods for analysis and chemiluminescent detection of nucleic acids using labeled probes, for example, solution hybridization assays, DNA detection in Southern blotting, RNA by Northern blotting, gene expression profiling, DNA sequencing, DNA fingerprinting, colony hybridizations and plaque lifts are all well established techniques. The label can be present as a direct conjugate with a probe oligonucleotide or capture oligonucleotide or it can be incorporated through indirect linking means using art-known methods. Examples of indirect linking means include using hapten-labeled oligonucleotides and labeled anti-hapten antibodies or biotinylated oligonucleotides and labeled avidin or labeled streptavidin. Such nucleic acid assays can be performed on a blotting membrane or in solution using oligonucleotides attached to solid surfaces including beads, tubes, microwells, magnetic particles, microarrays or test strips as are known in the art.

In another embodiment the present methods are used in determining the base sequence of a nucleic acid. The methods make use of labeled deoxyribonucleotides or labeled dideoxyribonucleotides. In one embodiment four parallel reaction mixtures are formed; in each reaction all of the four dNTPs, a primer, the template to be sequenced, and a polymerase are provided along with one of the four possible ddNTPs labeled in accordance with the present invention. Polymerase extension is allowed to proceed and the reactions separated electrophoretically according to known methods. The labeled sets of extension products are detected using one of the detection reactions described above and the patterns of differently sized fragments from each of the four reactions are combined to deduce the sequence. Labeled nucleotides can be prepared using labeling compounds of the invention and the four nucleotides. Label attachment can be achieved through the purine or pyrimidine base or through the terminal phosphate group of the triphosphate residue. In another embodiment four different labels can be used to differentially label the four ddNTPs. The labels can have different fluorescent moieties covalently linked to the compound of formula I that permit them to be resolved fluorometrically. In this embodiment one reaction can provide the information of the four reaction system described above. In another embodiment no dNTPs are used but rather a mixture of the four ddNTPs in either the four reaction/one label or one reaction/four label formats. This will provide the identity of one unknown base at the position immediately adjacent to the primer. Such an embodiment could be useful in identification of SNPs.

Use of the present chemiluminescent reaction for detection of labeled analytes, such as nucleic acids, proteins or antibodies, provides an advantage over most other chemiluminescent labeling methods. It has been found that the chemiluminescent-labeled analyte can undergo electrophoresis and be directly detected in gels such as acrylamide and agarose. The labeled analyte is not destroyed or triggered at the electrical potential and currents employed in the process as would be expected based on the prior art. This technique represents a significant advance in detection methodology by removing the need for a membrane transfer step and should be particularly well suited for detection of DNA sequencing ladders. In comparison to the labeling compounds disclosed in Applicants' U.S. Pat. Nos. 6,017,769 and 6,126,870, the present labeling compounds and labeled compounds present better stability. The present ketene dithioacetal labels (carbon-carbon double bond with two sulfur atoms at the terminal carbon) are markedly more stable in aqueous or protic solutions than the compounds with a sulfur atom and a phosphate group on the terminal carbon. Moreover, the absence of a phosphate group in the present labels provides increased flexibility in synthesis, particularly in preparing a compound bearing the useful N-hydroxysuccinimide group.

Another embodiment is the immunological detection of proteins in gels or by the technique of Western blotting. A sample containing a protein of interest as the analyte is subject to electrophoretic separation. The separated proteins are either detected directly in the gel or transferred to a blotting membrane such as a nitrocellulose or PVDF membrane by capillary action or with the aid of an electric field. Transferred protein is detected with either a labeled primary antibody or a specific primary antibody and a labeled secondary antibody which recognizes and binds to the primary antibody. Quantitative determination of the label reflects the presence of the analyte protein. To adapt the methods of the present invention for Western blotting, antibody is labeled with a chemiluminescent labeling compound of the present invention. Another embodiment uses biotinylated antibodies and chemiluminescent labeled avidin or unlabeled avidin and a biotin-chemiluminescent label conjugate.

Light emitted by the present method can be detected by any suitable means, including luminometers, x-ray film, high speed photographic film, a CCD camera or visually. Choice of the detection device will be governed by the application and considerations of cost, convenience, spectral sensitivity and need for a permanent record.

Multi-analyte assays can be performed using two or more distinguishable chemiluminescent labels concurrently to label different analytes. Appropriately chosen chemiluminescent labels may be independently detected on the basis of different emission wavelengths. Alternatively two or more different labels may be distinguishable by the time required to emit the light. Methods for chemiluminescent multi-analyte assays are disclosed in U.S. Pat. No. 5,656,207, the disclosure of which is incorporated herein by reference. Multi-analyte assays can also include detecting multiple regions of the same analyte, such as two different regions of a nucleic acid or two epitopes of an antigen. This type of assay is useful, for example, for detecting gene juxtapositions or for providing increased specificity of detection.

The invention is demonstrated further by the following examples which are illustrative and do not serve to limit the scope of the invention.

Examples

Example 1

Synthesis of Compound 1

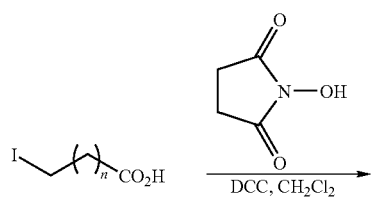

The iodocarboxylate NHS ester was synthesized by reacting the iodocarboxylic acids with N-hydroxy succinimide using DCC as the coupling reagent.

To a solution of dithioester B (1.808 g, 5.00 mmol) in anhydrous DMF (50 mL) was added NaH (60% in mineral oil, 0.200 g, 5.00 mmol) under argon. After 4 h at room temperature NHS 3-iodopropionate A (1.485 g, 5.00 mmol) was added and the resulting mixture was stirred overnight. DMF was removed in vacuo. Column chromatography with $CH_2Cl_2$/EtOAc (40:1) afforded 1.770 g of 1 as a yellow solid (yield 67%). $^1$H NMR (300 MHz, $CDCl_3$): δ 2.30 (s, 3H), 2.74 (t, 2H), 2.83 (s, 4H), 3.01 (t, 2H), 5.31 (s, 2H), 6.88(t, 2H), 7.07 (m, 2H), 7.11-7.18 (m, 3H), 7.27 (m, 4H), 7.82 (dd, 1H), 7.89 (dd, 1H) ppm.

Example 2

Synthesis of Compound 2

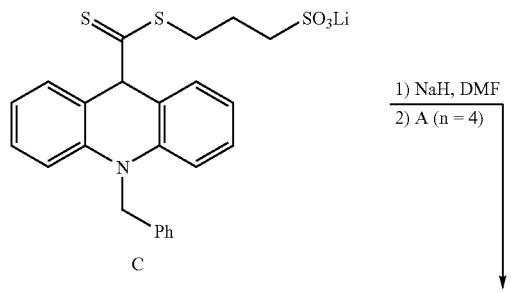

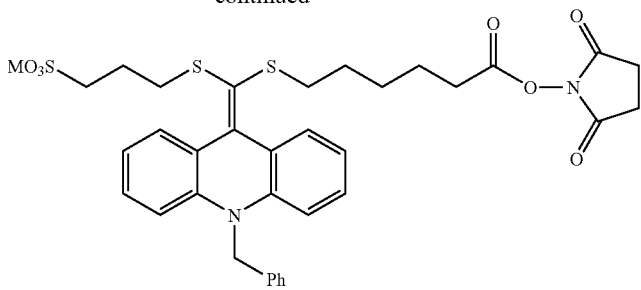

2

A mixture of dithioester C (0.692 g, 1.50 mmol) and NaH (60% in mineral oil, 0.060 g, 1.50 mmol) in anhydrous DMF (20 mL) was stirred under argon at room temperature for 4 hours, resulting a slightly cloudy solution. NHS 6 iodohexanoate A (0.661 g, 1.95 mmol) was then added in DMF (5 mL). After 16 h, DMF was removed in vacuo. To the residue was added 10 mL of acetone followed by 20 mL of ether. The supernatant was decanted. The precipitate was washed three times following the same procedures. After drying under vacuum, 1.200 g of 2 was obtained as a yellow solid. $^1$H NMR (300 MHz, CD$_3$OD): δ 1.15 (m, 2H), 1.33-1.47 (m, 4H), 2.01 (p, 2H), 2.38 (t, 2H), 2.67 (t, 2H), 2.75 (t, 2H), 2.82 (s, 4H), 2.88 (t, 2H), 5.32 (s, 2H), 6.88 6.93 (m, 2H), 7.00 (t, 2H), 7.08-7.28 (m, 7H), 7.83 (d, 1H), 7.92 (d, 1H) ppm.

Example 3

Synthesis of Compounds 3 and 4

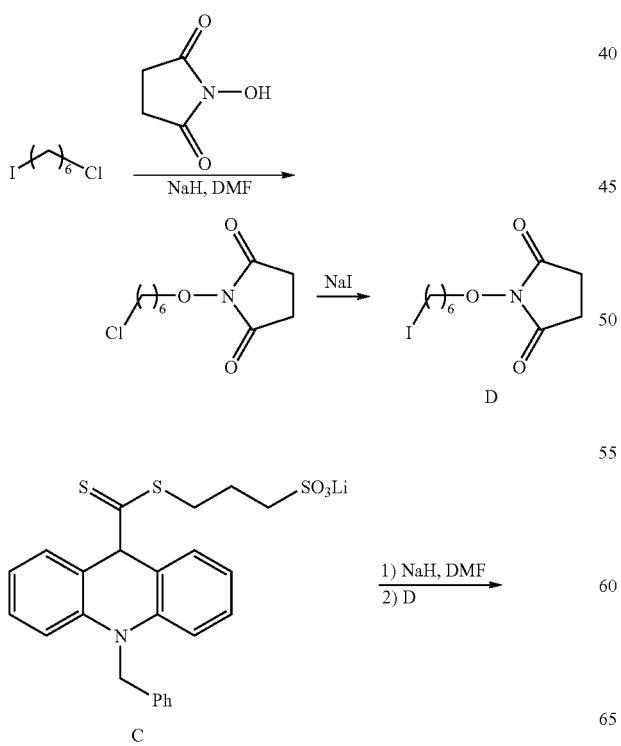

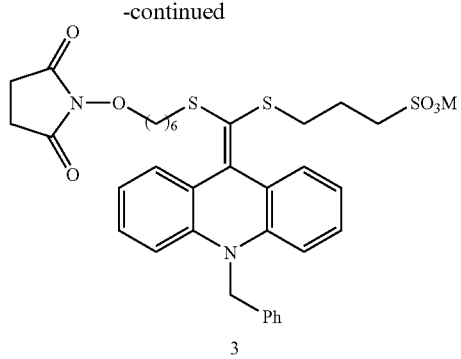

A mixture of dithioester C (1.00 g, 2.10 mmol) and NaH (60% in mineral oil, 0.087 g, 2.16 mmol) in anhydrous DMF (20 mL) was stirred under argon at room temperature for 4 hours, resulting in a slightly cloudy solution. N-6 iodohexoxysuccinimide D (0.82 g, 2.52 mmol) was then added in DMF (5 mL). The mixture was stirred over night after which DMF was removed in vacuo. The residue was washed four times with 30 mL of ether giving 1.35 g of 3.

Compound 3 (0.25 g) was dissolved in 5 mL of methanol to which was added 5.0 mL of 50% aq. NH2OH. After stirring the solution for 2 days, the solvents were evaporated under vacuum. The residue was washed with 6×20 mL of ether giving 0.21 g of 4. $^1$H NMR (300 MHz, CD$_3$OD): δ 1.14 (m, 4H), 1.40 (m, 4H), 1.94 (p, 2H), 2.65-2.71 (m, 4H), 2.84 (t, 2H), 3.55 (t, 2H), 5.31 (s, 2H), 6.88 (d, 2H), 6.98 (q, 2H), 7.10 (m, 4H), 7.12-7.27 (m, 3H), 7.85 (t, 2H) ppm.

Example 4

Synthesis of Compounds 5 and 6

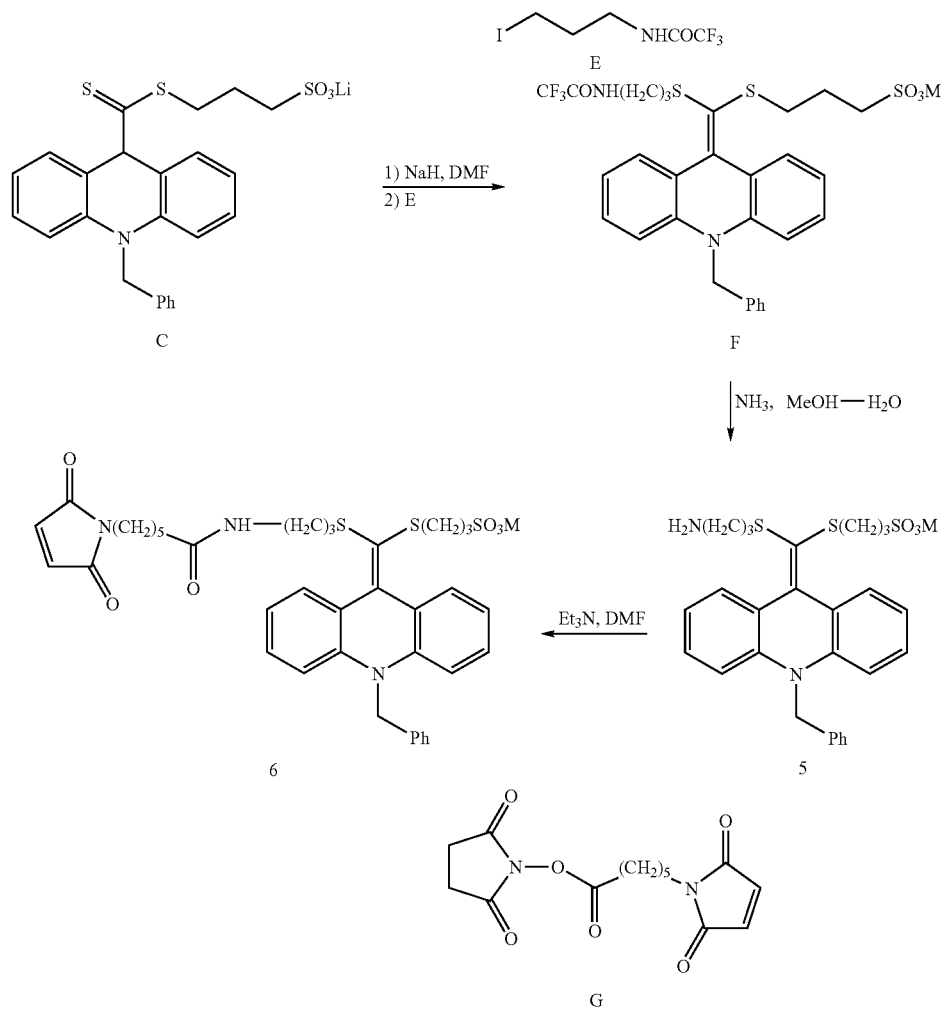

A mixture of dithioester C (1.32 g, 2.78 mmol) and NaH (60% in mineral oil, 0.114 g, 2.86 mmol) in 30 mL of anh. DMF was stirred under argon at room temperature for 4 hours. Compound E (1.014 g, 3.61 mmol) was then added in 10 mL of DMF. The mixture was stirred over night after which DMF was removed in vacuo. The residue was washed three times with 20 mL of ether giving 2.10 g of Compound F.

Compound F (2.25 g) was dissolved in a mixture of 15 mL of 7 N NH3 in MeOH and 10 mL of 28% aqueous ammonia solution. After 3 days of stirring, solvents were removed under vacuum. The residue was washed with ether (3×50 mL) and recrystallized with $H_2O$/2-propanol, giving 1.20 g of 5.

To a suspension of 5 (0.300 g, 0.563 mmol) in 9.0 mL of dry DMF was added 1.20 mL of triethylamine. The mixture was stirred for 5 min, giving a slightly cloudy solution. To this was added 6-maleimidohexanoic NHS ester (G 0.260 g, 0.843 mmol). A clear solution as resulted in 5 min. After 16 hrs, DMF was removed under vacuum. The residue was washed with ether (4×30 mL), then dissolved in MeOH (2 mL) and precipitated with ether (50 mL). A 0.400 g yield of 6 was obtained as a yellowish foam-like solid. $^1$H NMR (400 MHz, $CD_3OD$): δ 1.26 (t, 11H), 1.49-1.58 (m, 6H), 1.90 (p, 2H), 2.08 (t, 2H), 2.68 (m, 4H), 2.80 (t, 2H), 3.00 (t, 2H), 3.15 (q, 6H), 3.42 (t, 2H), 5.28 (s, 2H), 6.73 (s, 2H), 6.85 (d, 2H), 6.96 (m, 2H), 7.07 (m, 4H), 7.18-7.25 (m, 3H), 7.83 (m, 2H) ppm.

Example 5

Additional Labeling Compounds 7-12

The preparation of other exemplary labeling compounds listed below was disclosed in U.S. Pat. No. 6,858,733.

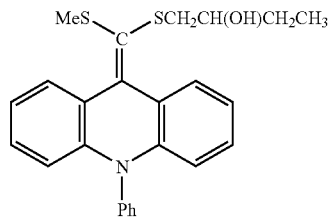

7

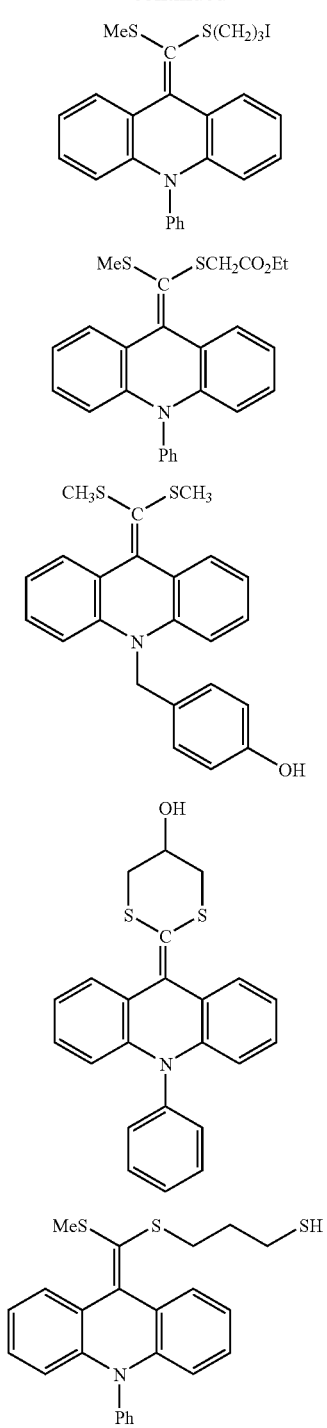

Example 6

Additional Labeling Compounds

Compounds 13 and 14 were prepared by a similar reaction sequence as was used in preparing 1 but starting with N-methylacridan and N-phenylacridan, respectively. In these structures M represents a positively charged counter ion, such as Li⁺ or Na⁺.

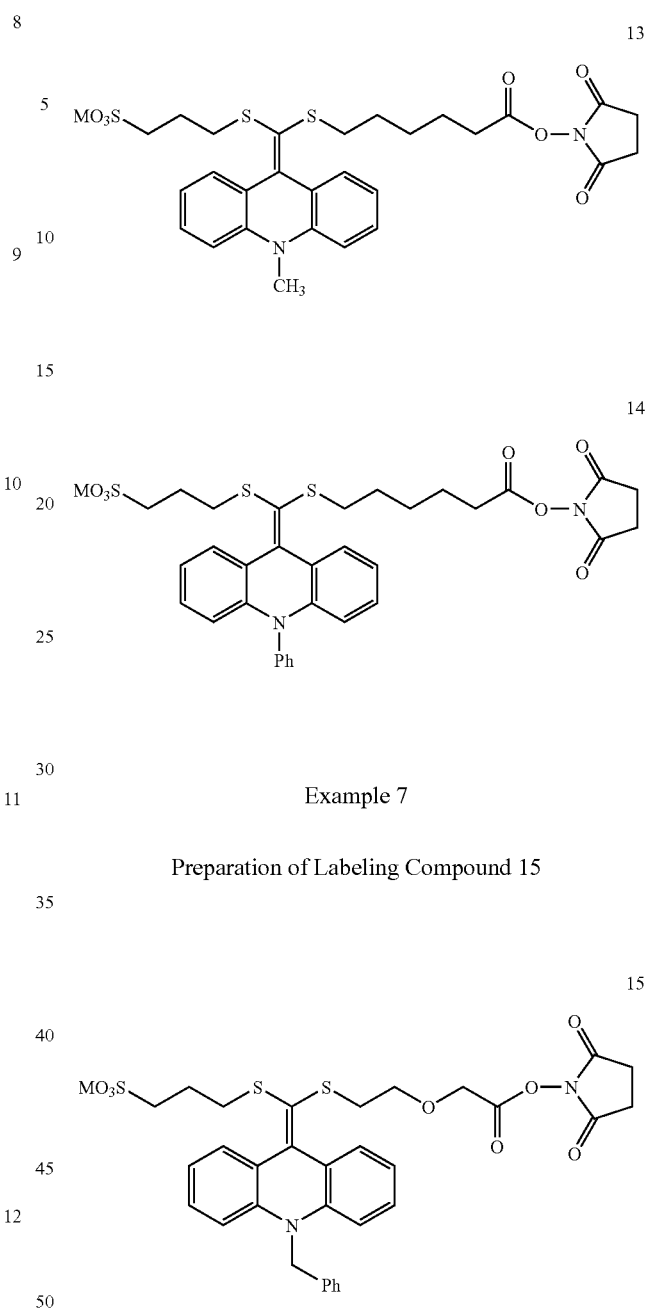

Example 7

Preparation of Labeling Compound 15

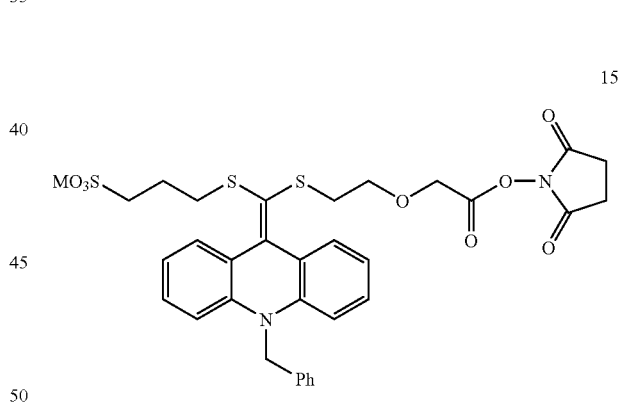

Compound C of Example 4 was S-alkylated, after formation of the enethiolate anion with NaH in DMF, with iodo NHS ester H. The product was purified by recrystallization from 2-propanol.

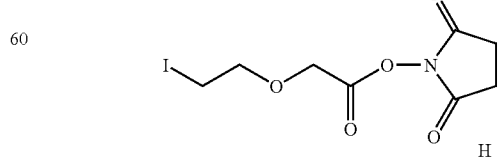

Example 8

Preparation of Labeling Compound 16

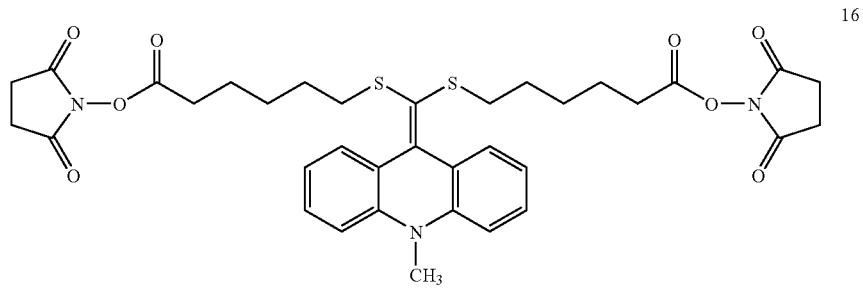 [SMILES: CN1c2ccccc2C(=C(SCCCCCC(=O)ON2C(=O)CCC2=O)SCCCCCC(=O)ON2C(=O)CCC2=O)c2ccccc21]

The bis(NHS ester) compound was synthesized by a reaction process beginning with reaction of the anion of N-methylacridan with $CS_2$ in THF, allowing the reaction to warm from −78° C. to room temperature, followed by addition of 6-iodohexanoic acid NHS ester and column chromatographic purification of the dithioester. A second alkylation with the iodo NHS ester was conducted in DMF with NaH as base to produce 16 which was also purified by column chromatography.

Example 9

Preparation of Labeling Compound 17

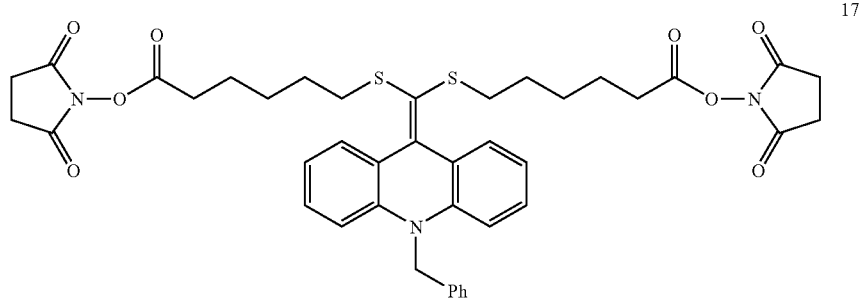 [SMILES: O=C(CCCCCSC(SCCCCCC(=O)ON1C(=O)CCC1=O)=C1c2ccccc2N(Cc2ccccc2)c2ccccc21)ON1C(=O)CCC1=O]

The bis(NHS ester) compound was synthesized by a reaction process beginning with reaction of the anion of N-benzylacridan with $CS_2$ in THF, allowing the reaction to warm from −78° C. to room temperature, followed by addition of 6-iodohexanoic acid NHS ester and column chromatographic purification of the dithioester. A second alkylation with the iodo NHS ester was conducted in DMF with NaH as base to produce 17 which was also purified by column chromatography.

Example 10

Labeling of Antibody

Mouse anti-TSH antibody was labeled with Compound 2 as follows. A 0.25 mg sample of antibody present as a 8.7 mg/mL stock solution was added to 0.5 mL of 0.1 M sodium borate pH 8.25 buffer. A 6.2 μL aliquot of a 2 mg/mL stock solution of Compound 2 in DMF (12.4 μg of 2) was added to the antibody solution. The mixture was vortexed briefly and shaken at 4° C. over night. The labeled antibody was purified from the unreacted label on a desalting column using PBS as elution buffer. Eleven 0.5 mL fractions were collected and assayed by chemiluminescence. Tubes 7-9 contained labeled antibody. A smaller loading of label can be obtained by using a smaller excess of labeling compound, e.g. a 3:1 ratio of label to antibody. Labeled antibody can be detected according to any of the methods of examples 11-13 below.

Example 11

Detection of Label with HRP and Peroxide

Compound 2 was detected by the following procedure. A 1 mg/mL stock solution of 2 in DMF was prepared (1.45 mM) and diluted 100× in 25 mM tris pH 8 buffer. Further dilutions were made in 25 mM tris pH 8 buffer containing 1.4 nM HRP. Three μL aliquots were assayed by addition of 100 μL of 25 mM tris pH 8 buffer containing 10 mM urea peroxide. The aliquots contained from $4.35 \times 10^{-14}$ to $4.35 \times 10^{-17}$ moles of Compound 2. A plot of the peak light intensity as a function of the amount of compound 2 was linear over this range.

Example 12

Detection of Label with Transition Metal and Peroxide

Compound 2 was detected by the following procedure. A 1 mg/mL stock solution of 2 in DMF was prepared (1.45 mM) and diluted 100× in 25 mM tris pH 8 buffer. Further dilutions were made in 25 mM tris pH 8 buffer. Three μL aliquots were assayed by addition of 100 μL of 25 mM tris pH 8 buffer containing 10 mM urea peroxide and 1 mM $CoCl_2$. The aliquots contained from $4.35 \times 10^{-14}$ to $4.35 \times 10^{-17}$ moles of Compound 2. A plot of the peak light intensity as a function of the amount of compound 2 was linear over this range.

Example 12

Detection of Model Label Compound by Reaction with Singlet Oxygen

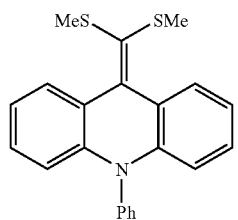

Compound 18 (33.3 mg) and polymer-bound Rose Bengal (10.1 mg) were suspended in 8 mL of MeOH. The suspension was cooled to −78° C. with an acetone/dry ice bath in a silvered Dewar. Oxygen was bubbled slowly through the suspension. The suspension was irradiated with a 400-watt Na lamp through a 5 mil Dupont Kapton™ filter. After 10 minutes of irradiation, an aliquot was removed and placed on dry ice. In a darkened room, the sample was allowed to warm and a brilliant blue light was observed for 15-20 seconds as the sample warmed. TLC (5% EtOAc/hexanes) showed residual starting alkene and the N-phenylacridone. The reaction sequence can be explained by the reaction scheme below.

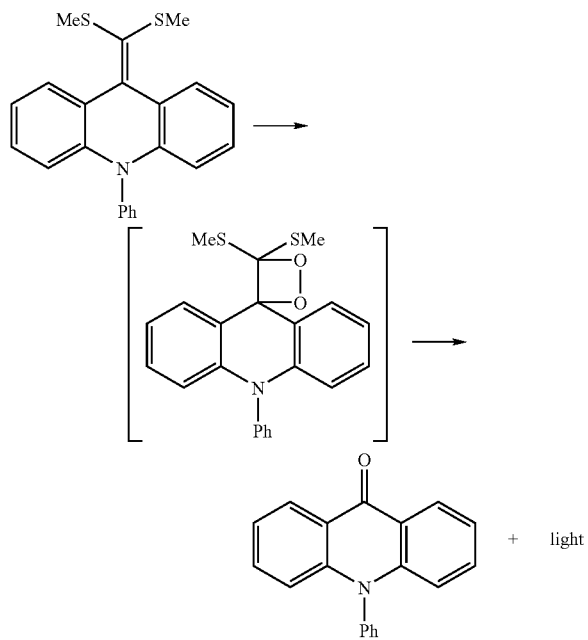

Similarly labeling compounds of formulas I-V and compounds labeled with these compounds can be photooxygenated and produce detectable chemiluminescence. While the example depicts discrete photooxygenation and chemiluminescent detection steps, it is unnecessary that they be performed separately, nor is it necessary for the photosensitized oxidation to be performed at −78° C.; temperatures up to room temperature may be employed.

The foregoing description and examples are illustrative only and not to be considered as restrictive. It is recognized that modifications of the specific compounds and methods not specifically disclosed can be made without departing from the spirit and scope of the present invention. The scope of the invention is limited only by the appended claims.

What is claimed is:

1. A method for detecting a labeled compound in a sample wherein the labeled compound comprises a compound linked to a chemiluminescent label, said labeled compound having the formula:

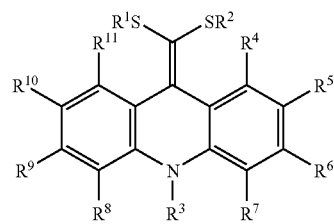

wherein each of $R^1$, $R^2$ and $R^3$ is selected from substituted or unsubstituted alkyl, substituted or unsubstituted alkenyl, substituted or unsubstituted alkynyl, substituted or unsubstituted aryl, substituted or unsubstituted aralkyl groups of 1-20 carbon atoms, wherein $R^1$ and $R^2$ can be joined together in a ring, $R^4$-$R^{11}$ are independently selected from hydrogen and substituents which do not interfere with the generation of chemiluminescence, and at least one of the groups $R^1$-$R^{11}$ is linked to the compound by means of a labeling substituent L-RG where L is a linking group and RG is a reactive group said method comprising:

a) reacting the labeled compound with a peroxide and a transition metal compound selected from transition metal ions, transition metal salts, or transition metal complexes for producing chemiluminescence from the chemiluminescent label; and b) detecting the chemiluminescence as an indication of the presence of the compound.

2. The method of claim 1 wherein the labeling substituent -L-RG is present as a substituent on $R^1$ or $R^2$.

3. The method of claim 1 wherein each of $R^4$-$R^{11}$ is a hydrogen atom.

4. The method of claim 3 wherein the labeling substituent -L-RG is present as a substituent on $R^1$, wherein $R^2$ is alkyl substituted with an $SO_3^-$ group, and wherein $R^3$ is selected from substituted or unsubstituted $C_1$-$C_4$ alkyl groups, phenyl, substituted or unsubstituted benzyl groups.

5. The method of claim 4 wherein L is selected from a bond, divalent groups and polyvalent groups containing from 1 to 30 non-hydrogen atoms selected from C, N, O, P and S atoms.

6. The method of claim 5 wherein RG is a reactive group selected from carboxyl, carboxyl ester, acid anhydride, acid chloride, acyl azide, aldehyde, chloroformate, amine, hydroxyl, hydrazine, hydrazide, hydroxylamine, isocyanate, isothiocyanate, sulfonyl chloride, $SO_2CH_2CF_3$, tosyl, maleimide, N-hydroxysuccinimide ester, aziridine, disulfide, azide, halogen,

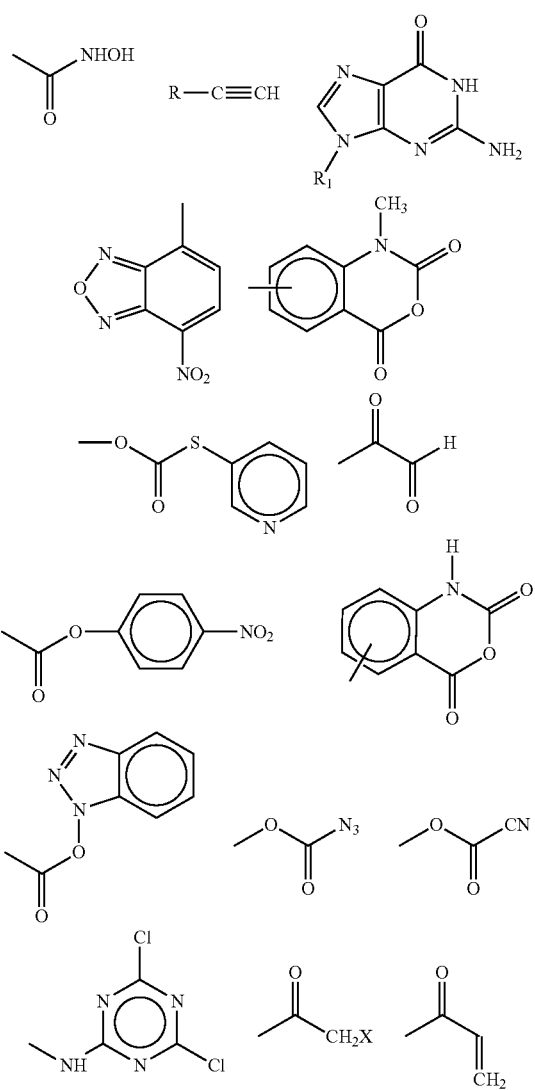
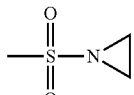
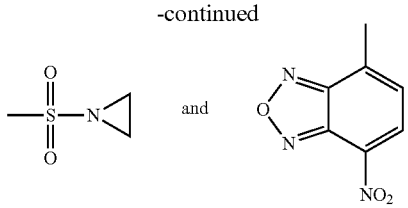
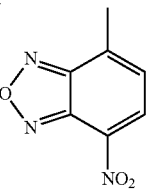

wherein X is selected from chlorine, bromine and iodine.

7. The method of claim 5 wherein the reactive group is selected from OH, $NH_2$, COOH, $SO_2CH_2CF_3$, N-hydroxysuccinimide ester, N-hydroxysuccinimide ether, and maleimide groups.

8. The method of claim 1 wherein the labeled compound comprises a labeled analyte or a specific binding pair member.

9. The method of claim 8 wherein the analyte is selected from drugs, hormones, pesticides, pesticide metabolites, DNA, RNA, oligonucleotides, antibodies, and antigens.

10. The method of claim 8 wherein the specific binding pair member is selected from antigens, antibodies, haptens, oligonucleotides, polynucleotides, avidin, streptavidin, hormones, receptors, lectins, carbohydrates, IgG, protein A, and nucleic acid binding proteins.

11. The method of claim 1 wherein the transition metal ion is selected from $Fe^{+2}$, $Fe^{+3}$, $Co^{+2}$, $Co^{+3}$, $Cu^{+2}$, $Ni^{+2}$, $Cr^{+3}$, $Zn^{+2}$ and $Mn^{+2}$.

12. The method of claim 11 wherein the transition metal is supplied at a concentration of $10^{-6}$ to $10^{-1}$ M and the peroxide is supplied at a concentration of $10^{-6}$ to $10^{-1}$ M.

13. The method of claim 12 wherein the peroxide can be hydrogen peroxide or a complex of hydrogen peroxide, urea peroxide, perborate or percarbonate.

* * * * *